United States Patent [19]
Haaga

[11] Patent Number: 6,162,203
[45] Date of Patent: Dec. 19, 2000

[54] CARGO DELIVERY NEEDLE

[76] Inventor: John R. Haaga, 4309 N. Hilltop, Chagrin Falls, Ohio 44022

[21] Appl. No.: 09/228,117

[22] Filed: Jan. 11, 1999

[51] Int. Cl.[7] ............................ A61M 5/32; A61M 5/178; A61M 5/00; A61B 10/00; A61B 19/00

[52] U.S. Cl. ................... 604/272; 604/164.06; 604/264; 600/567; 128/898

[58] Field of Search ..................................... 604/164, 264, 604/272, 500, 502, 506, 57; 128/898; 606/170, 171; 600/564, 567

[56] References Cited

U.S. PATENT DOCUMENTS

| | | |
|---|---|---|
| 4,669,473 | 6/1987 | Ricards et al. ........................... 128/334 |
| 4,936,835 | 6/1990 | Haaga . |
| 5,053,046 | 10/1991 | Janese . |
| 5,251,641 | 10/1993 | Xavier ..................................... 128/754 |
| 5,254,105 | 10/1993 | Haaga . |
| 5,290,310 | 3/1994 | Makower et al. . |
| 5,292,332 | 3/1994 | Lee . |
| 5,324,306 | 6/1994 | Makower et al. . |
| 5,388,588 | 2/1995 | Nabai et al. . |
| 5,394,887 | 3/1995 | Haaga . |
| 5,431,639 | 7/1995 | Shaw . |
| 5,437,631 | 8/1995 | Janzen . |
| 5,477,862 | 12/1995 | Haaga . |
| 5,483,972 | 1/1996 | Nabai et al. . |
| 5,487,392 | 1/1996 | Haaga . |
| 5,560,373 | 10/1996 | De Santis ................................ 128/753 |
| 5,716,375 | 2/1998 | Fowler . |
| 5,725,498 | 3/1998 | Janzen et al. . |
| 5,728,114 | 3/1998 | Evans et al. ............................. 606/148 |
| 5,741,223 | 4/1998 | Janzen et al. . |
| 5,980,548 | 11/1999 | Evans et al. ............................. 606/185 |
| 5,989,196 | 11/1999 | Chu et al. ................................ 600/567 |

*Primary Examiner*—Sharon Kennedy
*Assistant Examiner*—Michael J. Hayes
*Attorney, Agent, or Firm*—Vickers, Daniels & Young

[57] ABSTRACT

A cargo delivery device has coaxial, telescopically interengaged cargo delivery needle, an outer cannulas which are axially and rotatably displaceable relative to one another. The cargo delivery needle has a distal portion provided with a cargo recess for carrying a cargo to a site in a patient.

32 Claims, 6 Drawing Sheets

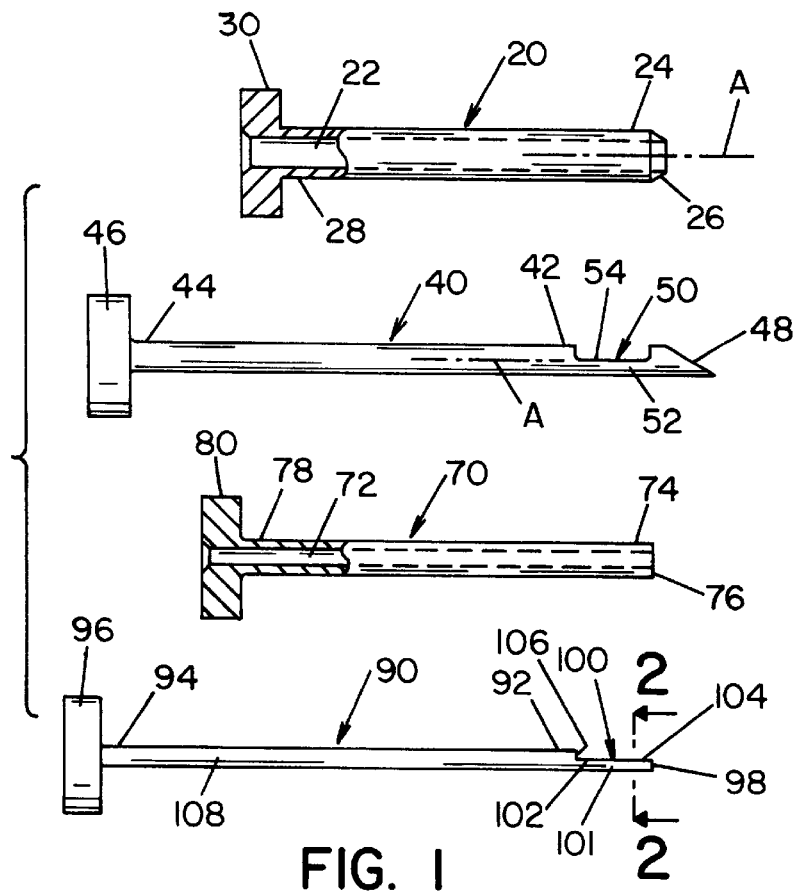
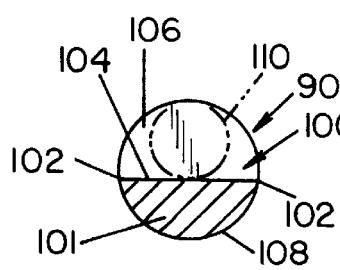
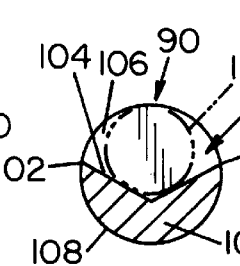
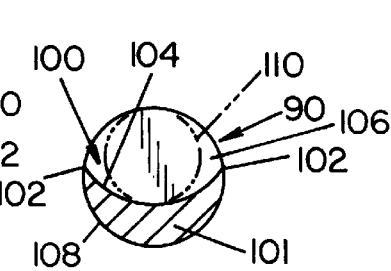
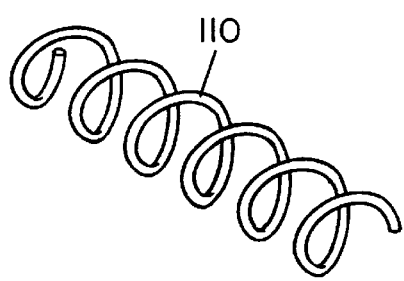
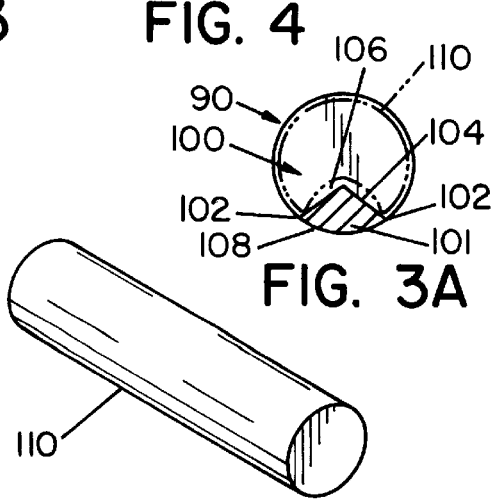

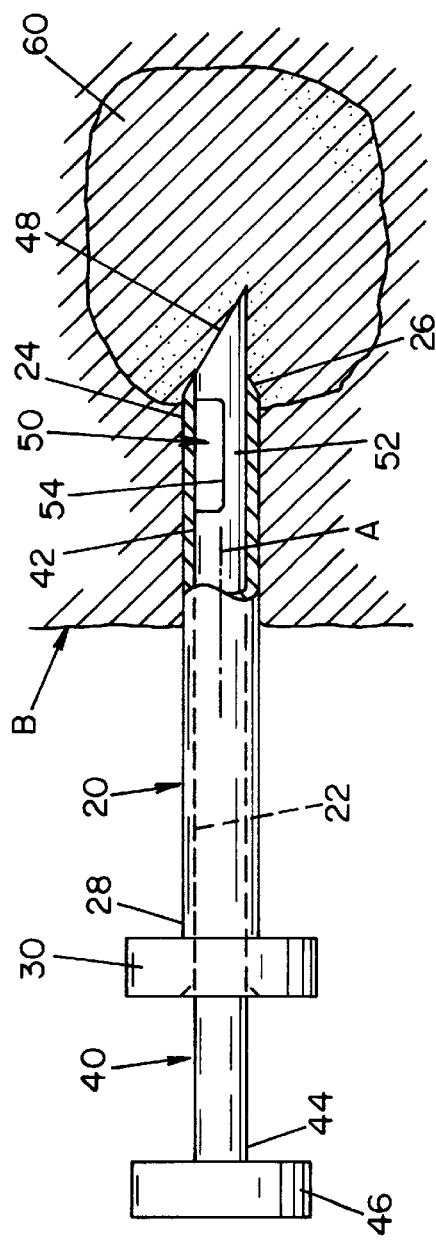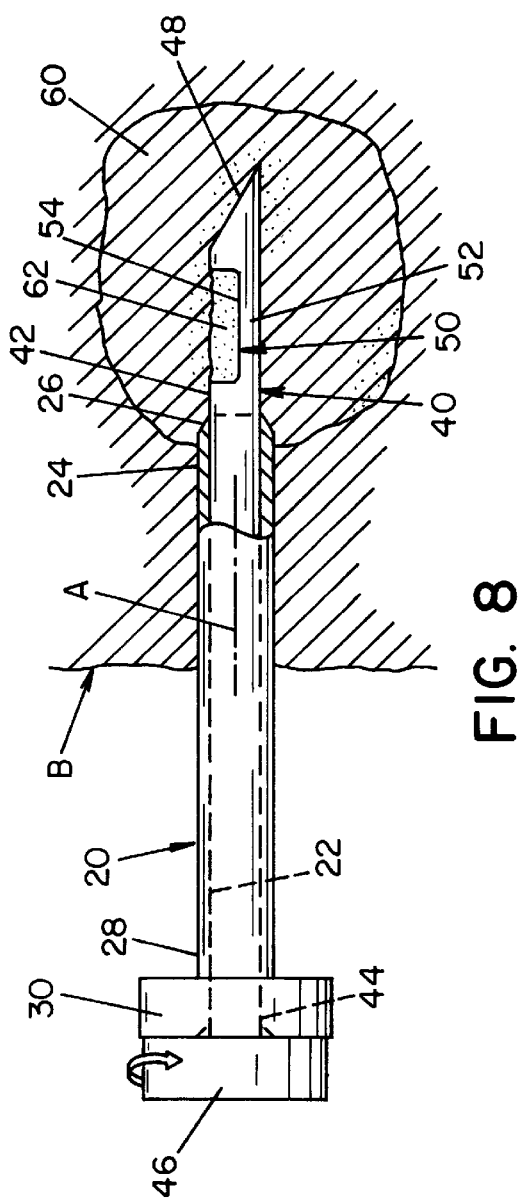

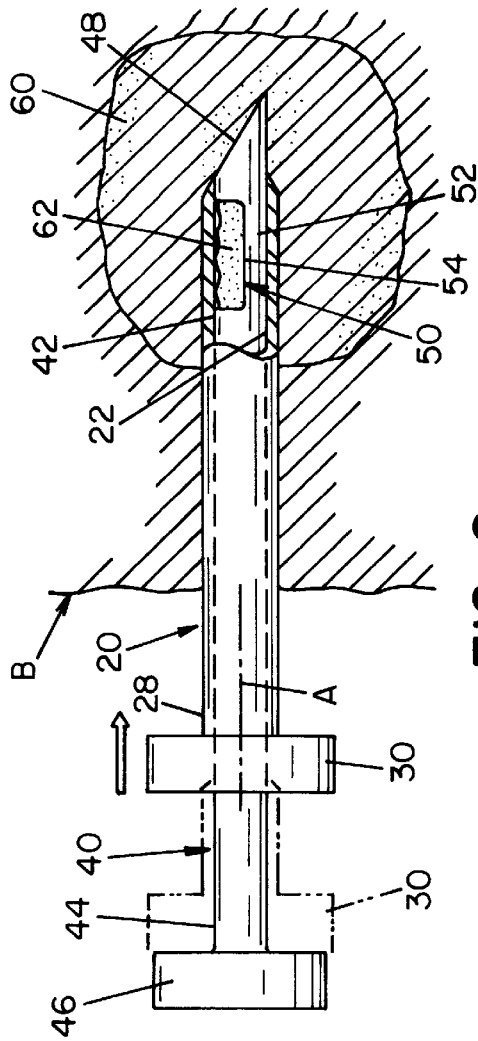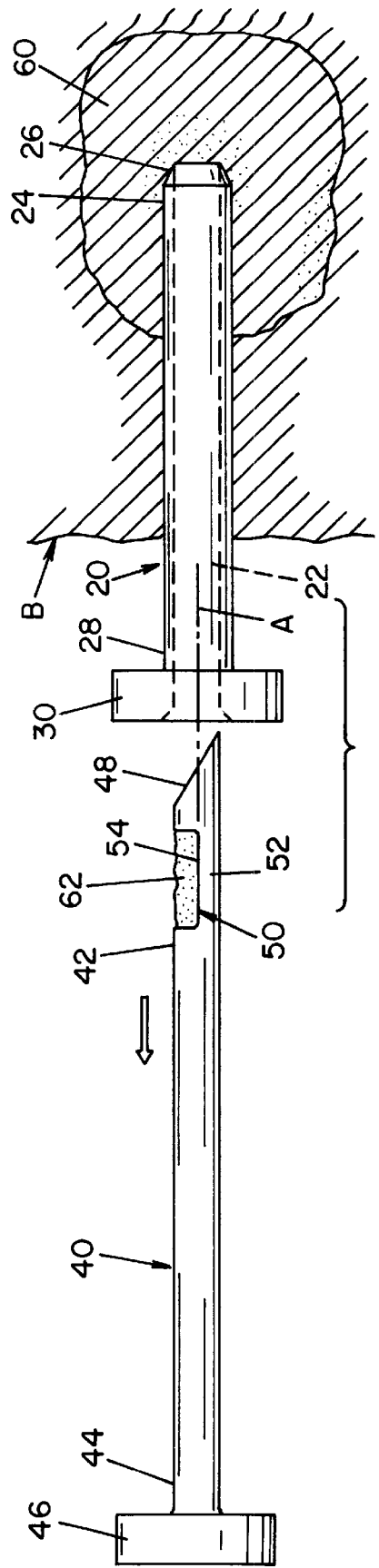
FIG. 9
FIG. 10

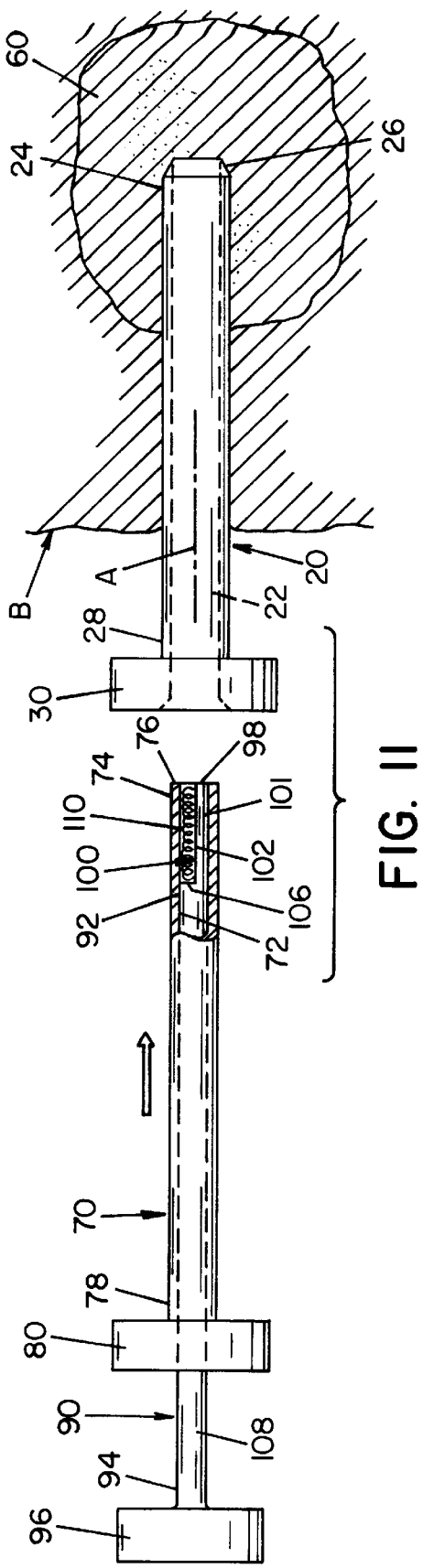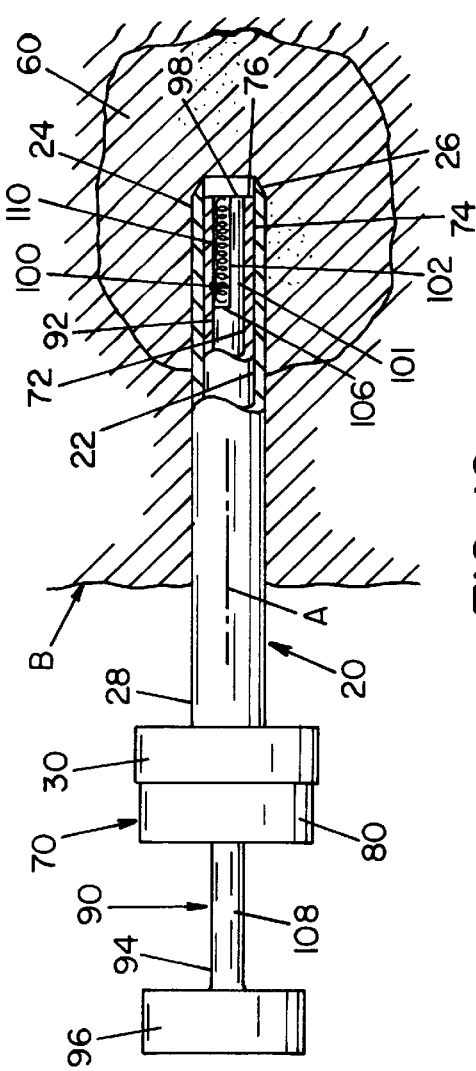

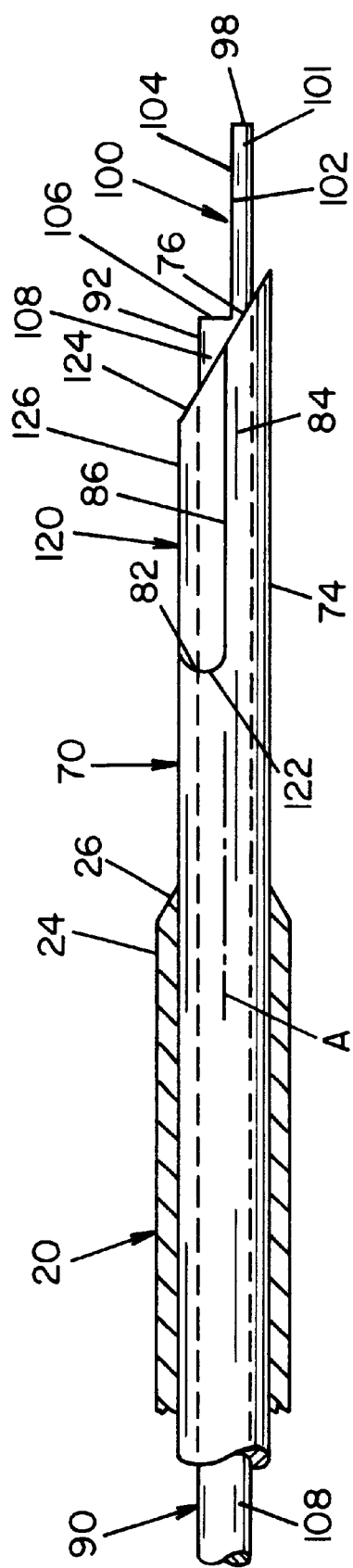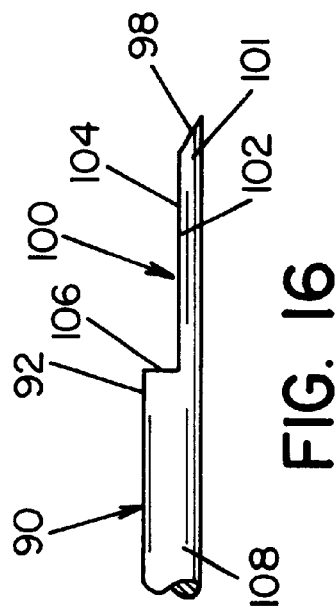

CARGO DELIVERY NEEDLE

This invention relates in general to surgical needles and, more particularly, to improvements in the delivery of materials into a body site of a patient.

INCORPORATION BY REFERENCE

My prior U.S. Pat. Nos. 4,708,147; 4,838,280; 4,936,835; 5,080,655; 5,195,988; 5,254,105; 5,330,445; 5,394,887; 5,447,502; 5,477,862; 5,487,392; 5,573,518; and 5,718,237 which disclose various type of biopsy needles are all incorporated herein by reference.

BACKGROUND OF THE INVENTION

The invention is particularly applicable to the delivery of materials such as medication, DNA, and tissue, and will be described in particular with reference thereto. It will be appreciated by those skilled in the art, however, that the invention has broader application and may be used for selective deposition of materials or selective extraction of tissue samples and the subsequent deposition of materials into living matter.

One type of biopsy needle which can be used in the present invention relates is a side cut needle such as the type commercially known as "Trucut" needles. Such a side cut needle includes a solid stylet telescopically received within an inner tubular cannula which in turn is telescopically received within an outer tubular cannula by which the stylet and inner tubular cannula are supported for axial and rotative displacement relative to one another and to the outer cannula. The side cut needle is inserted into a patient until the distal end of the outer cannula reaches the lesion where a biopsy specimen is to be taken. The stylet is then advanced relative to the outer and inner cannulas into the lesion to the biopsy site. The stylet is provided with a cutting recess in the distal portion thereof and, when the stylet reaches the biopsy site, the stylet is rotated so that a cutting edge of the cutting recess severs the tissue. The inner cannula is then advanced relative to the outer cannula and over the stylet to cut the tissue into the cutting recess and to cover the recess and thus entrap the specimen within the recess for removal from the site by retracting the stylet and inner cannula into the outer cannula and then withdrawing the needle from the patient.

In a number of my prior U.S. Pat. Nos. 4,708,147; 4,838,280; 4,936,835; 5,080,655; 5,195,988; 5,254,105; 5,330,445; 5,394,887; 5,447,502; 5,477,862; 5,487,392; 5,573,518; and 5,718,237, there is disclosed a side cut needle of the foregoing character in which the equivalent of the inner cannula referred to above is provided with a tubular sheath of a absorbable gelatin material or a non-bioabsorbable hemostatic collagen for minimizing bleeding of the patient from the biopsy site upon removal of the needle. In this respect, the hemostatic sheath is applied about the distal portion of the inner cannula and is advanced therewith into the lesion for the inner cannula to cover the cutting recess in the stylet which, as described above, is initially inserted into the lesion and rotated to sever a biopsy specimen to be removed from the lesion. In accordance with my earlier arrangements, the equivalent of the outer cannula referred to hereinabove is also inserted into the lesion and has a distal end adjacent the axially inner end of the hemostatic sheath for positioning the sheath in the location where the biopsy specimen was taken when the specimen is withdrawn therefrom. More particularly in this respect, when the biopsy specimen is cut and enclosed in the cutting recess as described above, the stylet and inner cannula are withdrawn or retracted relative to the outer cannula which is held stationary at the site, whereby the axially inner end of the sheath engages the outer cannula and is held in its position within the lesion as the inner cannula and stylet are retracted into the outer cannula. When the sheath is released from the inner cannula, the needle is withdrawn from the site of the lesion.

While the hemostatic sheath in my earlier arrangements served its intended purpose to minimize bleeding from the biopsy site by compressing the bleeding tissue surrounding the biopsy site and by swelling upon absorbing body fluid so as to increase the compressive effect, there were a number of disadvantages with respect to the structure and manipulation of the component parts of the biopsy needle in connection with obtaining a biopsy specimen.

These disadvantages were overcome in my later patents. The new biopsy needles were designed such that the distal portion of the inner cannula was provided with a recess which supports a hemostatic insert for displacement therewith into the biopsy site in conjunction with advancing the inner cannula over the cutting recess in the stylet of the needle following rotation thereof to sever a specimen at the site. Accordingly, when the needle is inserted in a patient's body to move the distal end of the distal portion of the outer cannula to a position adjacent the lesion, and the stylet is then extended relative to the outer cannula to penetrate the lesion and is rotated to sever a biopsy specimen therefrom, the inner cannula and the hemostatic insert supported thereon remain within the distal portion of the outer cannula, thus the hemostatic insert is advantageously protected from exposure to infectious micro-organisms prior to use and during use is protected from exposure to body fluids by the outer cannula during the needle inserting and specimen severing stages. The inner cannula and hemostatic insert arrangement minimized the diametrical dimension of the puncture in the lesion by the needle to that of the inner cannula in a standard side cut needle, thus to minimize the possibility of hemorrhagic complications. The biopsy needle also enables automated operation of the side cut needle through the use of well known "guns".

My biopsy needles disclosed in my previous patents provide an effective means for successfully obtaining tissue samples either by manual or automated techniques while reducing complications such with bleeding. However, there still exists a deficiency in the art relating to the delivery of a "cargo" to a specific site in the body. These "cargos" include, but are not limited to, gelform, angiographic coil, tissue, medication, DNA, or other like materials. In many medical techniques, it is essential to deliver materials to a specific site in the body. Many of these materials cannot be delivered by an injection, thus requiring surgery which is significantly more expensive, time consuming, and can be significantly more painful and lead to complications and infection.

Therefore, there is a need for a device that can efficiently and effectively deliver a variety of materials to a specific site in a body which reduces complications and bleeding and avoids the traditionally more evasive medical techniques.

SUMMARY OF THE INVENTION

In accordance with the present invention, there is provided a cargo delivery needle by which the foregoing disadvantages are overcome. The cargo delivery needle is designed to deliver a material to a specific site in a body. More particularly in accordance with the invention, the cargo delivery needle is provided with a cargo recess positioned at the distal portion of the needle. The cargo recess is designed to receive and maintain a material until the needle is positioned at the desired body site, at which site the material is delivered at the body site as the needle is retracted from the body site. The material may include tissue, DNA, medication, various medical devices, gelform, and the like. In one preferred embodiment, the cargo delivery needle is a longitudinally-extending cylindrical member having an outer surface, a proximal end, a distal end and a cargo recess at least closely adjacent to with the distal end. The cargo recess opens radially into the needle from the outer surface and has a bottom wall and a proximate wall between the bottom wall and outer surface. The cargo recess is radially spaced from the bottom wall and longitudinally extending from the proximate wall. In another preferred embodiment, the cargo recess is coterminous with the distal end of the needle. This design of the cargo recess provides a recess that extends from the proximate wall to the distal end of the needle. In yet another embodiment, the proximate wall of the cargo recess is non-tangentially positioned to the bottom wall. In such an arrangement, at least one portion of the proximate wall forms an acute angle with the bottom wall. This design of the proximate wall of the recess opening facilitates in maintaining the material in the recess opening until the material is deposited at the body site.

In accordance with another feature of the present invention, the bottom wall of the cargo recess is defined to facilitate the handling of the material in the recess until the material is delivered at the body site. The bottom wall is preferably designed to function as a platform and/or a cradle for the material in the recess. In one preferred embodiment, the bottom wall is substantially parallel to the longitudinal axis of the cargo delivery needle and substantially planar or flat in shape. The planar or flat bottom wall provides a stable surface for a variety of materials to be laid on the recess for transport to a body site. In another preferred embodiment, the bottom wall includes a groove or trough which includes a V-shape, inverted V-shape, partially polygonal shape, curvilinear shape, inverted curvilinear shape or the like. The groove or trough function to cradle the material in the recess to prevent undesired shifting of the material in the recess as the material is transported to a body site. As can be appreciated, the shape of the bottom wall can be selected to hold specifically sized and shaped materials to better ensure that such material are properly transported to the body site and that the material is properly oriented in the body site.

In accordance with yet another embodiment of the present invention, the cargo delivery needle is inserted into a body site after a biopsy has been taken at the body site. The taking of a biopsy at a body site prior to delivering material by the cargo delivery needle to the body site has several advantages. These advantages include, but are limited to, the removal of undesired tissue at a body site, defining the location of the deposited material in the body site and/or providing a space in the body site for depositing the material in the cargo delivery needle. The biopsy can be taken by a wide variety of biopsy needles.

In accordance with still yet another embodiment of the present invention, the cargo delivery needle in used in conjunction with a biopsy needle. In this regard, a biopsy is taken prior to the delivery of the material by the cargo delivery needle. Once the biopsy has been taken, the cutting needle or stylet and inner cannula, if used, are removed from the outer cannula and a delivery cannula and cargo delivery needle are inserted into the outer cannula. Using this arrangement, the outer cannula of the biopsy needle functions to position both the cutting needle and the cargo delivery needle in a body site. This arrangement advantageously reduces the need to insert multiple outer cannulas into a body site to access a particular body site; reduces additional penetration into the body site thereby reducing the amount of irritation, hemorrhaging and/or damage to the tissue about the body site; and facilitates in the depositing of material at the desired location in the body site. As can be appreciated, a wide variety of biopsy needles can be used in conjunction with the cargo delivery needle. In one preferred embodiment, the biopsy needle is similar to the biopsy needles disclosed in my prior patents which are incorporated herein by reference.

In accordance with still another embodiment of the present invention, the distal end of the cargo delivery needle is generally blunt to reduce hemorrhaging, cutting and/or irritation of the body site as the cargo delivery needle in positioned at the body site. The generally blunt cargo delivery needle is preferably used in conjunction with a biopsy needle. In one preferred embodiment the cargo delivery needle is inserted subsequent to the removal of a biopsy by a biopsy needle. The removal of tissue at the body site by the biopsy needle forms a region whereby the material in the cargo delivery needle can be deposited. Furthermore, the prior insertion of biopsy needle forms a precut channel for the subsequently inserted cargo delivery needle. As a result, the cargo delivery needle does not require a cutting surface to reach and deposit a material contained in the cargo recess at the body site.

In accordance with another embodiment of the present invention, a hemostatic insert is deposited at the body site with or subsequent to the material in the cargo recess being deposited at the body site. In one preferred embodiment, the hemostatic insert is positioned at least partially about a delivery cannula and is deposited in a body site by movement of the delivery cannula and/or by another component of the cargo delivery device. In accordance with this arrangement, the cargo delivery needle is positioned inside the delivery cannula and can be moved independently of the delivery cannula and hemostatic insert. In another preferred embodiment, the distal portion of the delivery cannula is provided with a recess which supports a hemostatic insert for displacement therewith into the biopsy site in conjunction with advancing the delivery cannula and cargo delivery needle. The cargo delivery needle and delivery cannula have corresponding extended and retracted positions relative to the outer cannula and, in the retracted positions prior to use, the distal portions of the cargo delivery needle and delivery cannula, and the insert carried by the latter, are within the distal portion of the outer cannula. The delivery cannula and cargo delivery needle are then extended relative to the outer cannula to penetrate into the body site. The delivery cannula and/or cargo delivery needle can include a cutting surface to cut a channel to the body site. Alternatively, the delivery cannula and/or cargo delivery needle include a blunt end for insertion into a previously cut channel to the body site. When the delivery cannula is advanced into the body site, the distal portion thereof adjacent the hemostatic insert support recess spans the distal portion of the cargo delivery needle. The insert is pushed into the body site by a portion of the recess in which it is supported. The hemostatic insert merely rests in the delivery cannula recess and is freely slidable axially outwardly of the distal end thereof whereby, upon withdrawal of the delivery cannula from the site, the insert remains in the body site. The cargo delivery needle and delivery cannula are displaced into their retracted positions relative to the outer cannula thereby depositing the material in the cargo recess and the hemostatic insert at the body site.

In still another preferred embodiment, the delivery cannula and hemostatic insert are preferably designed to minimize the diametrical dimension of the puncture in the channel to the body site, thus to minimize the possibility of hemorrhagic complications. In yet another preferred embodiment, the hemostatic insert in simply resting on the inner cannula for sliding displacement therefrom enables the insert to remain at the body site without the need for a pushing component to assure that the insert remains at the site and without the need for a special manipulating of the component parts of the needle to remove the insert therefrom. The latter advantageously enables automated operation of the needle through the use of well known "guns" for operating the latter.

In accordance with still another feature of the present invention, the material in the cargo recess of the cargo delivery needle is protected from exposure to infectious micro-organisms prior to use and during use are protected from exposure to body fluids during depositing of the material at the body site. In one preferred embodiment, the cargo recess of the cargo delivery needle is positioned within the delivery cannula and/or outer cannula until just prior to positioning the cargo recess at the body site. This design also facilitates in maintaining the material in the cargo recess until the cargo recess is positioned at the body for depositing the material at the body site. In another preferred embodiment, the delivery cannula, the hemostatic insert supported thereon, and the cargo delivery needle remain within the distal portion of the outer cannula until just prior to positioning such components at the body site. Thus, the hemostatic insert and material in the cargo recess are protected from exposure to infectious micro-organisms prior to use and during use are protected from exposure to body fluids by the outer cannula just prior to depositing of the material at the body site. In another preferred embodiment, the cargo recess of the cargo delivery needle is positioned within the delivery cannula and outer cannula until the material in the cargo recess is positioned at the body site. In this embodiment, the cargo delivery needle, the delivery cannula and the outer cannula are all positioned at the body site before the material in the cargo recess is delivered at the body site. The delivery cannula, the hemostatic insert, if used, and the cargo delivery needle remain within the distal portion of the outer cannula until the cargo and hemostatic insert, if used, are deposited at the body site as the delivery needle, delivery cannula and outer cannula are removed from the body site. Thus, the hemostatic insert and material in the cargo recess are protected from exposure to infectious micro-organisms exposure to body fluids by the outer cannula until being deposited at the body site. In still another preferred embodiment, the hemostatic insert facilitates in retaining the material deposited at the body site. In this regard, the material that is deposited at the body site is at least partially retained in the body site by depositing a hemostatic insert at least partially adjacent to the material deposited in the body site. The hemostatic insert functions to inhibit or prevent the migration of the deposited material from the body site.

In accordance with yet another embodiment of the present invention, the hemostatic insert is a bioabsorbable, non-bioabsorbable or semi-bioabsorbable material such as, for example, collagen, gelatin, cellulose, absorbable polymers and combinations thereof. Preferably, the insert is non-bioabsorbable collagen which is preferred because of its faster and greater swelling upon exposure to body fluids. In one preferred embodiment, the insert is semi-circular in cross-section and, upon exposure to body fluids, expands radially and circumferentially into a somewhat circular, solid plug configuration. The insert can also be of a bioabsorbable material such as gelatin which, as is well known, initially expands at the biopsy site to occlude the flow of blood therefrom and, subsequently, dissolves within the body. In either event, or in connection with the use of other material to form the hemostatic insert, the insert can be coated or otherwise provided with thrombin which, again as is well known, is a protein which promotes blood clotting. In another preferred embodiment, the hemostatic insert facilitates in the removal of the materials from the cargo recess. In this regard, the surface of the insert engages the material in the cargo recess and assists in at least partially retaining the material at the body site when the insert is deposited at the body site. Preferably the insert is designed to expand in the presence of body fluids. The expansion of the insert causes the insert to engage the material in the cargo recess and at least partially retain the material at the body site as the cargo delivery needle is retracted from the body site. In still another preferred embodiment, the hemostatic insert facilitates in retaining the material deposited at the body site. In this regard, the material that is deposited at the body site is at least partially retained in the body site by depositing a hemostatic insert at least closely adjacent to the material deposited in the body site. The hemostatic insert functions to inhibit or prevent the migration of the deposited material from the body site.

In accordance with still yet another embodiment of the present invention, the cargo delivery needle is used in conjunction with one or more components of a standard biopsy needle. The dimensions of the cargo delivery needle are selected such that the cargo delivery needle can be inserted into an outer or inner cannula of a standard biopsy needle. This design of the cargo delivery needle reduces or eliminates the need for completely removing a biopsy needle prior to delivering a cargo to a body site, thus simplifying the material delivery procedure, better insuring that the material is properly inserted into the body site, and reducing additional cutting of the patient and/or increased damage or irritation of the tissue about the body site. In one preferred embodiment, the cargo delivery needle is positioned in a delivery cannula. The delivery cannula and cargo delivery needle are then inserted into an outer cannula that has been previously inserted into a patient and positioned adjacent to or at the body site, which outer cannula was previously used in conjunction with a cutting stylet to remove a tissue sample from the body site.

It is accordingly a primary object of the present invention to provide a material delivery needle having the capability of depositing a material into a body site.

Another object of the present invention is the provision of a delivery needle having a cargo recess for delivering a material to a specific location in a body site.

Yet another object of the present invention is the provision of a delivery needle which can be used in conjunction with one or more components of a standard biopsy needle to delivery a material into a body site.

Still another object of the present invention is the provision of a delivery needle which can be used in conjunction with a standard biopsy needle to delivery a material into a body site after a biopsy has been taken from the body site.

Still yet another object of the present invention is the provision of a delivery needle that has a cargo recess shaped to retain, support and/or cradle a material in the cargo recess.

Yet another object of the present invention is the provision of a delivery needle which reduces hemorrhaging, irritation and/or damage to tissue about the body site when delivering material to the body site.

A further object of the present invention is the provision of a delivery needle which protects the material in the cargo recess until just prior to the material being delivered at the body site.

Another object of the present invention is the provision of a delivery needle which includes a hemostatic insert to be deposited at or adjacent to a body site.

Still another object of the present invention is the provision of a delivery needle which includes a hemostatic insert which assists in retaining materials at the body site as the cargo delivery needle is retracted from the body site.

Yet another object of the present invention is the provision of a delivery needle in which the outer cannula, delivery cannula, and cargo delivery member as individual components of the needle are structured and structurally interrelated in a manner which accommodates automated operation of the needle by a gun, for the latter purpose, as well as manual operation by providing the proximal portions of the needle components with handle elements by which the needle components can be manually manipulated.

These objects and other features of the present invention will become apparent to those skilled in the art from a reading and understanding of the following detailed description of the specification taken together with the accompanying drawings.

BRIEF DESCRIPTION OF THE DRAWINGS

The invention may take physical form in certain parts and arrangement of parts, a preferred embodiment of which will be described in detail and illustrated in the accompanying drawings which form a part hereof and wherein:

FIG. 1 is a sectional side elevation view of the components of a biopsy needle and a cargo delivery device in accordance with the invention;

FIG. 2 is a cross-sectional view of the cargo delivery needle along line 2—2 of FIG. 1;

FIGS. 3, 3A, and 4 are cross-sectional views of alternate embodiments of the cargo delivery needle;

FIGS. 5–6 are perspective views of cargos that can be positioned in the cargo recess of the cargo delivery needle;

FIGS. 7–10 are side elevation views, partially in section, showing the various positions of the component parts of a biopsy needle as a biopsy sample is taken of the inner cannula of the needle and the hemostatic;

FIGS. 11–14 are side elevation views, partially in section, showing the various positions of the component parts of the cargo delivery device as a cargo is delivered at a body site;

FIGS. 15 is a side elevation view, partially in section, of an alternate embodiment of the cargo delivery device; and FIGS. 16 is a side elevation view of the end of a cargo delivery needle.

DESCRIPTION OF THE PREFERRED EMBODIMENT

Figure 13:
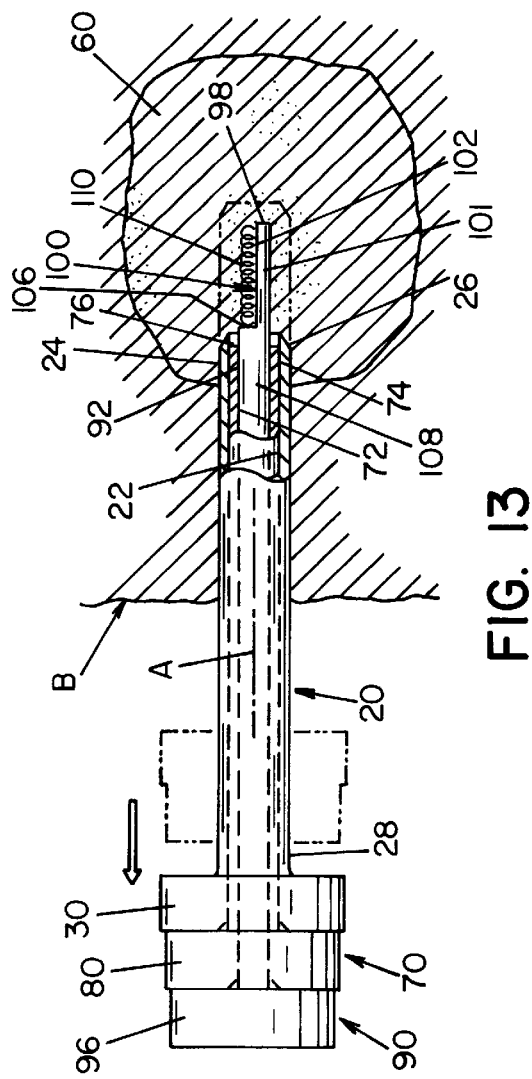

Referring now in greater detail to the drawings, wherein the showings are for the purpose of illustrating a preferred embodiment of the invention only, and not for the purpose of limiting the invention, FIG. 1 illustrates the individual component parts of a biopsy needle and a cargo delivery device in accordance with the present invention, and FIGS. 7–14 illustrate the component parts in assembled relationship prior to and during the use of the biopsy needle and the cargo delivery device. More particularly, the biopsy needle includes an outer cannula 20 as shown in FIG. 1, and a solid circular stylet 40. Outer cannula 20 is circular in cross-section, has an axis A and a circular passageway 22 therethrough. The outer cannula 20 and the stylet 40 are coaxial when assembled and, accordingly, these components are illustrated in the drawings and described hereinafter as having a common axis A. Outer cannula 20 further includes a distal portion 24 having a distal end 26, which is preferably tapered, and a proximal portion 28 which extends from distal portion 24 and includes a handle 30 by which the needle is held during use.

Stylet 40 is solid and circular in cross-section having a diameter which provides for the stylet to be received in passageway 22 of outer cannula 20 and supported therein for axial and rotative displacement relative thereto. Stylet 40 includes a distal portion 42 and a proximal portion 44 extending axially inwardly therefrom. Proximal portion 44 of stylet 40 is provided with a handle 46 to facilitate manual manipulation of the stylet relative to the outer cannula. The axially outer end of distal portion 42 of stylet 40 is beveled to provide a distal tip or end 48, and the distal portion is radially and axially cut away at a location spaced axially inwardly from distal end 48 to provide a specimen cutting recess 50 and a solid portion 52 of the stylet spanning the recess. Recess 50 includes axially extending cutting edges 54 for severing a specimen at the biopsy site during use of the needle.

When assembled, stylet 40 is displaceable between retracted and extended positions relative to outer cannula 20 and, prior to use, is in the retracted positions thereof shown in FIG. 7 and in which distal portion 42 of the stylet is disposed within distal portion 24 of outer cannula 20. Stylet 40 is illustrated in the drawings as being oriented relative to outer cannula 20 such that the planes of the distal ends thereof are coplanar, thus minimizing irritation and discomfort to a patient upon insertion of the needle into the patient's body. Prior to use of the needle and during initial insertion thereof into a patient's body, the outer cannula protects the stylet from infectious micro-organisms and minimizes exposure of the stylet to body fluids upon insertion of the needle.

The biopsy needle can include an inner cannula, not shown. The inner cannula and arrangement of the inner cannula with respect to the outer cannula and stylet is disclosed in my prior patents, which are incorporated herein. If an inner cannula is used, the inner cannula is circular in cross-section and has an outer diameter which provides for the inner cannula to be received in passageway 22 of outer cannula 20 and supported therein for axially sliding and rotative displacement relative thereto. The inner cannula has a circular passageway therethrough and includes a distal portion having a distal end and a proximal portion extending axially inwardly from the distal portion. The proximal portion of the inner cannula includes a handle by which the inner cannula is adapted to be manually displaced relative to outer cannula 20. The distal end of the distal portion of the inner cannula is provided by beveling the axially outer end, which beveling provides a cutting tip at the distal end of the inner cannula.

In use, the stylet is in the retracted position inside the outer cannula, as shown in FIG. 7. The needle is inserted into the body B of a patient until the distal ends 26, 48 of the outer cannula 20 and stylet 40, respectively, are adjacent a lesion 60 from which a biopsy specimen 62 is to be taken. When so positioned, stylet 40 is displaced axially inwardly relative to outer cannula 20 from its retracted position to its extended position in which specimen cutting recess 50 is located at the biopsy site in lesion 60 as shown in FIG. 8. Stylet 40 is then rotated about axis A, as shown in FIG. 8, to sever a tissue specimen at the biopsy site, and outer cannula 20 is then displaced axially inwardly relative to stylet 40 from its retracted position to its extended position shown in FIG. 9. During such movement of outer cannula 20, distal end 26 cuts the tissue at the biopsy site into tissue cutting recess 50 of stylet 40 and, in passing axially across the latter recess, distal portion 24 radially captures the specimen therein. When the tissue specimen has been captured in recess 50 as described above, stylet 40 is withdrawn from the lesion relative to outer cannula 20, as shown in FIG. 10, after which the stylet is withdrawn from the patient. The outer cannula remains in the body of the patient.

Referring now to FIG. 1, the cargo delivery components include a delivery cannula 70 and a cargo delivery needle 90. The delivery cannula 70 is circular in cross-section and has an outer diameter which provides for the delivery cannula to be received in passageway 22 of outer cannula 20 and supported therein for axially sliding and rotative displacement relative thereto. Delivery cannula 70 has a circular passageway 72 therethrough and includes a distal portion 74 having a distal end 76 and a proximal portion 78 extending axially inwardly from the distal portion 74. The proximal portion of the delivery cannula includes a handle 80 by which the delivery cannula is adapted to be manually displaced relative to outer cannula 20.

Cargo delivery needle 90 is solid and circular in cross-section having a diameter which provides for the needle to be received in passageway 72 of delivery cannula 70 and supported therein for axial and rotative displacement relative thereto. Cargo delivery needle 90 includes a distal portion 92 and a proximal portion 94 extending axially inwardly therefrom. The proximal portion 94 of delivery needle 90 is provided with a handle 96 to facilitate manual manipulation of the delivery needle relative to the outer cannula and delivery cannula. The axially outer end of distal portion 92 of cargo delivery needle 90 is generally blunt to provide a distal tip or end 98, and the distal portion 92 is radially and axially cut away at a location axially inwardly from distal end 98 to provide a cargo recess 100 and a solid portion 101 of the cargo delivery needle spanning the cargo recess. Cargo recess 100 includes axially extending edges 102 and a bottom wall 104 there between for retaining a cargo 110 in the cargo recess, which extends from distal end 98 and terminates at proximate wall 106 spaced proximately from distal end 98.

Referring to FIGS. 2, 3, 3A and 4, the cross-section of the distal end 98 of cargo delivery needle 90 is illustrated. FIG. 2 illustrates the cargo recess having a bottom wall 104 that lies in a plane generally parallel to the axis of the cargo delivery needle wherein a cargo 110 lies. FIG. 3 illustrates the cargo recess having a bottom wall 104 that is generally V-shaped wherein a cargo 110 lies. FIG. 3A illustrates the cargo recess having a bottom wall 104 that has a generally inverted V-shape wherein a cargo 110 lies. FIG. 4 illustrates the cargo recess having a bottom wall 104 that forms an arc between the two edges 102 of the cargo delivery needle wherein a cargo 110 lies. As can be appreciated, additional shapes of the bottom wall can be used. FIGS. 5 and 6 illustrate two types of cargo 110. FIG. 5 illustrates cargo 110 having a coil-like structure such as an angiographic coil. FIG. 6 illustrates cargo 110 having a cylindrically shaped structure such as gelform, tissue, medication, DNA, or other like materials.

When assembled, cargo delivery needle 90 is disposed in passageway 72 of delivery cannula 70, as shown in FIG. 11.

A cargo 110 is positioned in cargo recess 100 of the cargo delivery needle 90 prior to cargo delivery needle being disposed in delivery cannula 70. Outer cannula 20 is positioned in body B and distal portion 24 is positioned in lesion 60 due to the removal of a biopsy, as described above. Referring now to FIG. 12, cargo delivery needle 90 and delivery cannula 70 are displaceable between retracted and extended positions relative to outer cannula 20 and, prior to use, are in the retracted positions thereof shown in FIG. 12 and in which distal portions 74 and 92 of the delivery cannula and cargo delivery needle, respectively, are disposed within distal portion 24 of outer cannula 20. Cargo delivery needle 90 and delivery cannula 70 are illustrated in the drawings as being oriented relative to outer cannula 20 such that the planes of the distal ends thereof are generally flush. Prior to use of the cargo delivery needle and delivery cannula and during initial insertion thereof into a patient's body, the outer cannula protects the cargo delivery needle and the delivery cannula from infectious micro-organisms and minimizes exposure of the cargo delivery needle and the delivery cannula to body fluids upon insertion of the needle.

Figure 14:
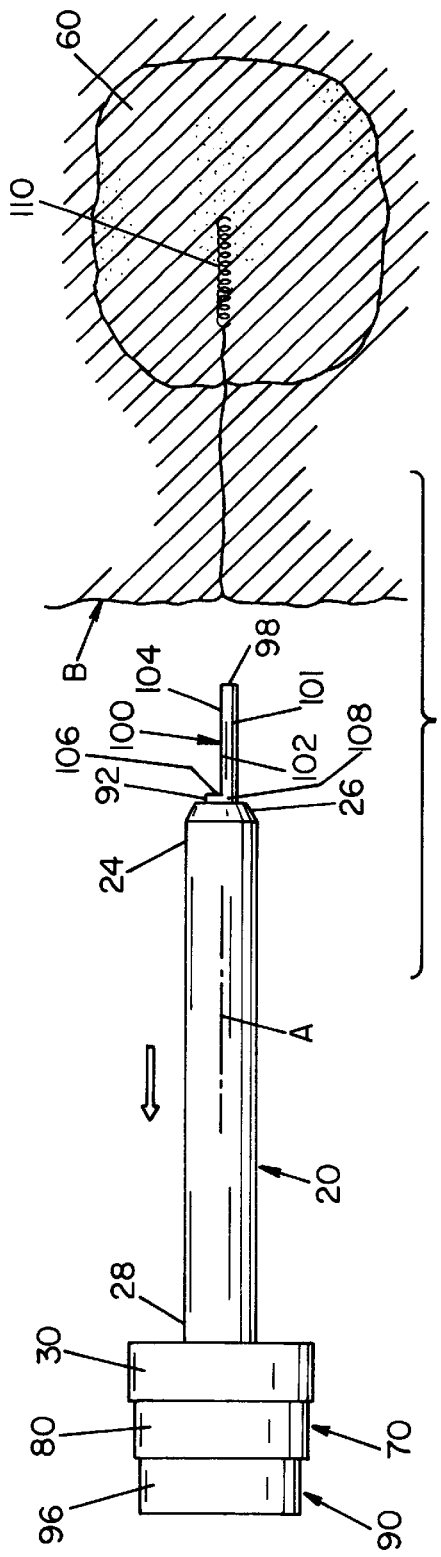

In use, the cargo delivery needle and the delivery cannula are in the retracted position inside the outer cannula wherein the distal ends 26, 76 and 98 of outer cannula, delivery cannula and cargo delivery needle are positioned in lesion 60. Cargo delivery needle is designed such that handle 96 is spaced from handles 80 and 30 of delivery cannula and outer cannula, respectively. When so positioned, outer cannula 20 and delivery cannula 70 are displaced axially inward relative to cargo delivery needle 90 in which the distal portion 92 of the cargo delivery needle remains at the biopsy site while the distal ends 26 and 76 of the outer cannula and delivery cannula are retracted from the biopsy as shown in FIG. 13. The delivery cannula is retracted until handle 80 contacts handle 96 of cargo delivery needle 90. Cargo 110 is shown in FIG. 13 as being exposed to the biopsy site. Once cargo 110 is exposed to the biopsy site, the cargo delivery needle, delivery cannula and outer cannula are withdrawn from the lesion, as shown in FIG. 14, therein depositing cargo 110 in the biopsy site.

A modification of the delivery cannula 70 is illustrated in FIG. 15. The delivery cannula has the upper portion of the distal portion 74 radially and axially cut away to provide a hemostatic insert 120 supporting recess 82 and an arcuate wall 84 having circumferentially spaced apart, axially extending side edge 86. Distal end 76 is beveled; however, the distal end need not be beveled. Preferably, axially extending side edge 86, of recess 82 lie in a diametrical plane through axis A, whereby the arcuate wall is semi-circular in cross-section.

Hemostatic insert 120 is preferably formed of collagen and, in the embodiment illustrated, is semi-circular in cross-section and has circumferentially spaced apart axially extending side edges, one of which is in contact with side edge 86 of recess 82. Hemostatic insert 120 further includes a circumferentially extending inner edge, 122 which engages against axially inner end edge of recess 82, and a circumferentially extending axially outer end edge 124. While the latter edge is shown as being beveled so as to be coplanar with the edge of distal end 76 of distal portion 74, the insert could have an axially outer end transverse to axis A. Hemostatic insert 120 has a radially outer surface 126 preferably having a radius of curvature corresponding to that of the outer surface 108 of delivery cannula 70. Outer surface 126 is dimensioned relative to axis A so as to provide for the insert, when on the distal portion of the delivery cannula, to be received in distal portion 24 of outer cannula 20 when the component parts are in the assembled positions thereof, as shown in FIG. 15. Hemostatic insert 120 has a radially inner surface dimensionally interrelated with axis A and cargo delivery needle 90 so as to allow the cargo delivery needle to slide relative thereto during displacement of the cargo delivery needle relative to the delivery cannula. Simultaneous with the foregoing delivery of cargo 110 at the biopsy site, hemostatic insert 120 is deposited adjacent or into the biopsy site when delivery cannula is withdrawn from the biopsy site. When hemostatic insert 120 is deposited adjacent or into the biopsy site in the foregoing manner, the hemostatic insert is exposed to body fluids and the material of the hemostatic insert absorbs body fluid and quickly begins to expand or swell, thus to compress the bleeding tissue surrounding the biopsy site to minimize bleeding therefrom. The preferred material for the hemostatic insert is collagen because of the quickness and the extent to which the material swells upon absorbing body fluids. In this respect, the hemostatic collagen insert will progressively expand radially and circumferentially such that the opposite ends become circumferentially constricted to form a generally circular configuration. The material continues to swell and the ends of the insert continue to become more constricted circumferentially, and such further expansion produces a substantial solid plug adjacent to or in the biopsy site which, through such swelling and distortion from its initial configuration, prevents the flow of blood from the site. Collagen is non-bioabsorbable and, accordingly, remains in the biopsy site as opposed to dissolving in the manner of a bioabsorbable gelatin.

Referring now to FIGS. 15 and 16, a modified cargo delivery needle is illustrated. FIG. 15 discloses the proximate wall 106 of cargo recess 100 as being non-perpendicular to bottom wall 104 of the cargo recess. This design of the proximate wall facilitates retaining materials in the cargo recess. FIG. 16 illustrates, a modified distal end of the cargo delivery needle. The distal end of the cargo delivery needle is beveled to allow the cargo delivery needle to cut a passageway to a cargo delivery site. The beveled end of the cargo delivery needle is preferably used when the cargo is delivered to a site in which a passageway to the delivery site has not been cut.

While considerable emphasis has been placed herein on the preferred embodiments, it will be appreciated that other embodiments can be made and that many changes can be made in the preferred embodiment without departing from the principles of the present invention. In this respect, for example, the hemostatic insert can have a circumferential contour and dimension other than the preferred contour and semi-circular dimension relative to the diameter of the delivery cannula. The latter is preferred to optimize displacement of the insert from the distal portion of the inner cannula following the extraction of a biopsy specimen and to optimize the cross-sectional area of the insert upon swelling thereof and thus the insert's ability to occlude the flow of blood from the biopsy site. Further, it will be appreciated that the hemostatic insert supporting recess in the distal portion of the inner cannula could be defined by a radially and axially extending recess in the outer surface of the inner cannula which does not extend completely through the wall thereof as in the preferred embodiment. Yet further, it will be appreciated that the proximate wall of the cargo recess can be shaped to facilitate in retaining the cargo in the cargo recess until the cargo is positioned at a delivery site. Still further, while the outer cannula, stylet, delivery cannula, and cargo delivery needle are illustrated and described herein as being provided with handles for manual manipulation of the component parts relative to one another, it will be appreciated that the components are adaptable to automated operation through the use of a "gun" for this purpose.

These and other modifications of the preferred embodiment, as well as other embodiments of the present invention, will be obvious to those skilled in the art from the disclosure of the preferred embodiment herein, whereby it is to be distinctly understood that the foregoing descriptive matter is to be interpreted merely as illustrative of the present invention and not as a limitation.

Having thus described the invention it is claimed:

1. A cargo delivery needle comprising a longitudinally-extending member being substantially cylindrical and having an axis, an outer surface, a proximal end, a distal end and a cargo recess, said cargo recess being coterminous with said distal end for delivering a cargo at a site, said cargo recess opening radially into said member from said outer surface and said distal end of said needle, said cargo recess having a bottom wall, a proximate wall, and a pair of bottom edges, said cargo recess extending from said distal end toward said proximal end and terminating at said proximal wall, said cargo recess extending radially from said outer surface into said longitudinally-extending member and terminating at said bottom wall, said bottom wall intersecting said outer surface at each one of said pair of bottom edges such that said bottom edges are parallel to said axis.

2. A cargo delivery needle as defined in claim 1, wherein said distal end being substantially blunt.

3. A cargo delivery needle as defined in claim 2, wherein said bottom wall being substantially planar.

4. A cargo delivery needle as defined in claim 2, wherein said bottom wall being substantially V-shaped.

5. A cargo delivery needle as defined in claim 2, wherein said bottom wall being curvilinear.

6. A cargo delivery needle as defined in claim 1, wherein said bottom wall being substantially planar.

7. A cargo delivery needle as defined in claim 1, wherein said bottom wall being substantially V-shaped.

8. A cargo delivery needle as defined in claim 1, wherein said bottom wall being curvilinear.

9. A cargo delivery device for delivering a cargo to a specific site in a patient, comprising an outer cannula having an axis, a delivery cannula coaxial with and relatively displaceably received in said outer cannula, a cargo delivery member coaxial with and relatively displaceably received in said delivery cannula, each said delivery and outer cannula and said cargo delivery member having a distal portion including a distal end and a proximal portion extending from said distal portion, said delivery cannula and said cargo delivery member being individually axially displaceable relative to said outer cannula, each being displaceable between a retracted and an extended position, in said retracted position each of said distal portions being stationed within the distal portion of said outer cannula, and in said extended position each of said distal portions being stationed axially outwardly from the distal end of said outer cannula and thereby being delivered into said site, said cargo delivery member including a longitudinally-extending member being substantially cylindrical and having an axis, an outer surface, a proximal end, a distal end, and a cargo recess, said cargo recess being coterminous with said distal end for delivering a cargo at a site, said cargo recess opening radially into said member from said outer surface in said distal end of said needle, said cargo recess having a bottom wall, a proximate wall, and a pair of bottom edges, said cargo recess extending from said distal end toward said proximal end and terminating at said proximal wall, said cargo recess extending radially from said outer surface into said longitudinally-extending member and terminating at said bottom wall, said bottom wall intersecting said outer surface at each one of said pair of bottom edges such that said bottom edges are parallel to said axis.

10. A cargo delivery device as defined in claim 9, wherein said bottom wall of said cargo recess is substantially planar.

11. A cargo delivery device as defined in claim 9, wherein said distal end of said cargo delivery member being substantially blunt.

12. A cargo delivery device as defined in claim 11, wherein said bottom wall of said cargo delivery member is substantially planar.

13. A cargo delivery device as defined in claim 11, wherein said bottom wall of said cargo delivery member is substantially V-shaped.

14. A cargo delivery device as defined in claim 11, wherein said bottom wall of said cargo delivery member is curvilinear.

15. A cargo delivery device as defined in claim 9, wherein said bottom wall of said cargo delivery member being substantially V-shaped.

16. A cargo delivery device as defined in claim 9, wherein said bottom wall of said cargo delivery member being curvilinear.

17. A cargo delivery device as defined in claim 9, wherein said distal portion of said delivery cannula includes an arrangement to maintain said cargo in said cargo recess of said cargo delivery member.

18. A cargo delivery device as defined in claim 17, wherein at least a portion of said proximate wall of said cargo delivery member being inclined at an acute angle relative to said bottom wall of said cargo delivery member.

19. A cargo delivery device as defined in claim 9, including a hemostatic insert being separable from said delivery cannula or said cargo delivery member to remain at said body site upon removal of said delivery cannula or said cargo delivery member from said body site.

20. A cargo delivery device as defined in claim 19, wherein said hemostatic insert is supported on the distal portion of said delivery cannula and is separable from said distal portion of said delivery cannula to remain at said site upon removal of said distal portion of said delivery cannula from said site.

21. A cargo delivery device as defined in claim 19, wherein said hemostatic insert comprising a hollow, cylindrical plug having a longitudinally extending axis and a longitudinally extending opening along said axis, said plug being arcuate transverse said axis and occludable to inhibit the flow of fluids from said site when exposed to fluid from said site.

22. A cargo delivery device as defined in claim 19, wherein said hemostatic insert is comprised of collagen.

23. A cargo delivery device as defined in claim 19, wherein said hemostatic insert includes thrombin.

24. A cargo delivery device as defined in claim 23, wherein said hemostatic insert is comprised of collagen.

25. A method for depositing a material to a body site comprising the steps of:
 a) providing a delivery needle and an outer cannula co-axially receiving said delivery needle, said delivery needle comprising a longitudinally-extending member being substantially cylindrical and having an axis, an outer surface, a proximal end, a distal end, and a cargo recess, said cargo recess being coterminous with said distal end for delivering a cargo at a site, said cargo recess opening radially into said member from said outer surface and said distal end of said needle, said cargo recess having a bottom wall, a proximate wall, and a pair of bottom edges, said cargo recess extending from said distal end toward said proximal end and terminating at said proximal wall, said cargo recess extending radially from said outer surface into said longitudinally-extending member and terminating at said bottom wall, said bottom wall intersecting said outer surface at one of said pair of bottom edges such that said bottom edges are parallel to said axis;
 b) moving said outer cannula into a patient to a point at least closely adjacent said body site where said material is to be deposited;
 c) moving said delivery needle to said body site;
 d) depositing said material in said cargo recess at said body site; and
 e) withdrawing said outer cannula and said delivery needle from said patient.

26. The method as defined in claim 25, wherein said outer cannula being inserted adjacent said body site prior to receiving said delivery needle.

27. This method as defined in claim 25, including the step of depositing a hemostatic insert during or subsequent to said material being deposited at said body site.

28. This method as defined in claim 25, wherein said delivery needle includes said longitudinally-extending member and a delivery cannula co-axially receiving said member.

29. The method as defined in claim 25, wherein said bottom wall of said member is substantially planar.

30. The method as defined in claim 25, wherein said distal end of said member being substantially blunt.

31. The method as defined in claim 30, wherein said bottom wall of said member is substantially planar.

32. The method as defined in claim 25, wherein said at least a portion of said proximate wall of said cargo recess being incline at an acute angle relative to said bottom wall.

* * * * *